(12) United States Patent
Miyama et al.

(10) Patent No.: US 9,975,105 B2
(45) Date of Patent: May 22, 2018

(54) SYSTEM FOR PRODUCING OXYGENATE AND METHOD FOR PRODUCING OXYGENATE

(71) Applicants: SEKISUI CHEMICAL CO., LTD., Osaka (JP); RENAISSANCE ENERGY RESEARCH CORPORATION, Kyoto (JP)

(72) Inventors: Toshihito Miyama, Tsukuba (JP); Tomoaki Nishino, Tsukuba (JP); Osamu Okada, Osaka (JP); Tamotsu Nonouchi, Kyoto (JP)

(73) Assignees: SEKISUI CHEMICAL CO., LTD., Osaka (JP); RENAISSANCE ENERGY RESEARCH CORPORATION, Kyoto (JP)

( * ) Notice: Subject to any disclaimer, the term of this patent is extended or adjusted under 35 U.S.C. 154(b) by 0 days. days.

(21) Appl. No.: 14/416,374

(22) PCT Filed: Jul. 23, 2013

(86) PCT No.: PCT/JP2013/069879
§ 371 (c)(1),
(2) Date: Jan. 22, 2015

(87) PCT Pub. No.: WO2014/017470
PCT Pub. Date: Jan. 30, 2014

(65) Prior Publication Data
US 2015/0182939 A1    Jul. 2, 2015

(30) Foreign Application Priority Data

Jul. 23, 2012 (JP) .................................. 2012-162789
Feb. 27, 2013 (JP) .................................. 2013-037934

(51) Int. Cl.
*C07C 29/158* (2006.01)
*B01J 19/24* (2006.01)
(Continued)

(52) U.S. Cl.
CPC ........... *B01J 19/245* (2013.01); *B01J 21/063* (2013.01); *B01J 21/08* (2013.01); *B01J 23/6562* (2013.01);
(Continued)

(58) Field of Classification Search
CPC ....... C07C 29/158; C07C 45/49; C07C 31/08; C07C 47/06; C07C 27/00; C07C 29/141;
(Continued)

(56) References Cited

U.S. PATENT DOCUMENTS 4,199,521 A    4/1980  Kaplan et al.
4,476,247 A    10/1984 Pesa et al.
(Continued)

FOREIGN PATENT DOCUMENTS

CN    1724151    *  1/2006
CN    101455966     6/2009
(Continued)

OTHER PUBLICATIONS

Machine generated English language translation of JP2012001441, p. 1-18.*
(Continued)

*Primary Examiner* — Jafar Parsa
*Assistant Examiner* — Amy C Bonaparte
(74) *Attorney, Agent, or Firm* — Wenderoth, Lind & Ponack, L.L.P.

(57) ABSTRACT

A system for producing an oxygenate, comprising: a desulfurization apparatus for contacting a raw material gas comprising hydrogen and carbon monoxide with a desulfurizing agent comprising copper; and a synthesis apparatus for
(Continued)

contacting the raw material gas treated by the desulfurizing apparatus with an oxygenate-synthesis catalyst comprising rhodium.

2 Claims, 6 Drawing Sheets

(51) Int. Cl.
| | |
|---|---|
| C07C 45/49 | (2006.01) |
| C01B 3/58 | (2006.01) |
| B01J 37/03 | (2006.01) |
| B01J 21/06 | (2006.01) |
| B01J 23/60 | (2006.01) |
| B01J 23/80 | (2006.01) |
| B01J 35/10 | (2006.01) |
| B01J 37/02 | (2006.01) |
| C07C 29/141 | (2006.01) |
| B01J 21/08 | (2006.01) |
| B01J 23/656 | (2006.01) |

(52) U.S. Cl.
CPC ........... *B01J 23/80* (2013.01); *B01J 35/1019* (2013.01); *B01J 35/1038* (2013.01); *B01J 35/1042* (2013.01); *B01J 35/1061* (2013.01); *B01J 37/0201* (2013.01); *B01J 37/031* (2013.01); *C01B 3/58* (2013.01); *C07C 29/141* (2013.01); *C07C 29/158* (2013.01); *C07C 45/49* (2013.01); *B01J 37/033* (2013.01); *B01J 2219/24* (2013.01); *C01B 2203/045* (2013.01); *C01B 2203/0485* (2013.01)

(58) Field of Classification Search
CPC .... B01J 19/245; B01J 21/063; B01J 2219/24; B01J 23/656; B01J 23/6562; B01J 23/80; B01J 35/1019; B01J 35/1038; B01J 37/0201; B01J 37/031; B01J 37/033; C01B 2203/045; C01B 2203/0485; C01B 3/58; Y02P 20/52
USPC .......................................... 518/705; 422/630
See application file for complete search history.

(56) References Cited

U.S. PATENT DOCUMENTS

| | | | |
|---|---|---|---|
| 4,521,387 A | 6/1985 | Broecker et al. | |
| 4,537,909 A | 8/1985 | Lin et al. | |
| 2005/0123462 A1* | 6/2005 | Hansen | ................... B01D 53/02 423/220 |
| 2012/0071697 A1* | 3/2012 | Ichikawa | .............. B01J 23/6562 568/885 |

FOREIGN PATENT DOCUMENTS

| | | | |
|---|---|---|---|
| EP | 0 021 443 | | 1/1981 |
| EP | 0243052 | * | 10/1987 |
| JP | 61-36730 | | 8/1986 |
| JP | 6-154593 | | 6/1994 |
| JP | 2003-201262 | | 7/2003 |
| JP | 2007-16185 | | 1/2007 |
| JP | 2009-532483 | | 9/2009 |
| JP | 2012-1441 | | 1/2012 |
| JP | 2012001441 | * | 1/2012 |
| WO | 2007/117590 | | 10/2007 |
| WO | WO 2010092819 | * | 8/2010 |
| WO | WO 2012/063034 | * | 5/2012 |

OTHER PUBLICATIONS

Machine generated English language translation of JP 2012001441, p. 1-16, obtained May 20, 2016.*
Casey ("Ch. 5: Reagents: Purification and Handling" p. 43-73 and "Ch. 8: Carrying Out The Reaction" p. 94-140, Advanced Practical Organic Chemistry, 1990).*
Deutschmann (" Heterogeneous Catalysis and Solid Catalysts, 2. Development and Types of Solid Catalysts" Ullmann's Encyclopedia of Industrial Chemistry, DOI: 10.1002/14356007.o05_o02, Oct. 15, 2011, p. 483-549).*
International Search Report dated Oct. 15, 2013 in International (PCT) Application No. PCT/JP2013/069879.
Extended European Search report dated Jul. 15, 2016 in European Patent Application No. 13823862.1.
Third Office Action dated Jul. 27, 2016 in Chinese Patent Application No. 201380048557.6, with English translation.

* cited by examiner

SYSTEM FOR PRODUCING OXYGENATE AND METHOD FOR PRODUCING OXYGENATE

TECHNICAL FIELD

The present invention relates to a system for producing an oxygenate and a method for producing an oxygenate.

Priorities are claimed on Japanese Patent Application No. 2012-162789, filed Jul. 23, 2012, and Japanese Patent Application No. 2013-37934, filed Feb. 27, 2013, the contents of which are incorporated herein by reference.

BACKGROUND ART

There is ongoing progress toward widespread replacement of petroleum with bioethanol as an alternative fuel. Bioethanol is produced mainly through saccharification and fermentation of sugarcane or corn. In recent years, a technique is being developed to produce bioethanol from wood-based biomass and plant-based biomass (which are also referred to as cellulosic biomass) such as wood waste or unused portions of crops such as rice straw, which do not compete with foods and feeds.

In order to produce bioethanol from cellulosic biomass as a raw material by a conventional ethanol fermentation method, it is necessary to saccharify the cellulose. As a saccharification method, there are known a method using concentrated sulfuric acid, a method using diluted sulfuric acid and enzyme, and a hydrothermal saccharification method; however, there are still many problems to be solved in order to produce bioethanol at a low cost.

Meanwhile, there is a method in which cellulosic biomass is converted to a mixed gas containing hydrogen and carbon monoxide, from which ethanol is synthesized. With this method, an attempt is made to efficiently produce bioethanol from cellulosic biomass to which the application of ethanol fermentation is difficult. In addition, raw materials which can be used in this method are not limited to the wood-based biomass and the plant-based biomass, but also include various organic materials such as animal biomass derived from carcasses or feces of animals, garbage, waste paper and waste fiber.

As a method for obtaining an oxygenate such as ethanol, acetaldehyde or acetic acid from a raw material gas containing hydrogen and carbon monoxide, for example, there is known a method in which the raw material gas is contacted with a catalyst comprising rhodium, an alkali metal and manganese (see, for example, Patent Document 1).

Further, as a method in which a raw material gas generated from biomass is converted to ethanol, there is proposed an ethanol production method comprising a step of removing a sulfur-containing compound from a raw material gas (see, for example, Patent Document 2).

CITATION LIST

Patent Documents

Patent Document 1: Japanese Examined Patent Application Publication No. Sho 61-36730
Patent Document 2: Japanese Unexamined Patent Application Publication (Translation of PCT Application) No. 2009-532483

DISCLOSURE OF INVENTION

Problems to be Solved by the Invention

As a result of studies made by the present inventors, it has been found that the production of an oxygenate from a raw material gas such as a gaseous biomass using a rhodium-containing catalyst suffers from a rapid lowering of catalyst activity due to the presence of a sulfur content in the raw material gas, resulting in the lowering of production efficiency of an oxygenate.

It is generally known that the sulfur content of gaseous biomass can be reduced to 1 ppm or less by a desulfurization method such as a pressure swing adsorption (PSA) method or a wet method using sodium hydroxide or the like.

However, the conventional desulfurization methods cannot effectively suppress the lowering of activity of a rhodium-containing catalyst.

The purpose of the present invention, in view of the above, is to provide a system for producing an oxygenate whereby the production of an oxygenate can be performed for a long term in spite of the use of a rhodium-containing catalyst.

Means to Solve the Problems

The oxygenate production system of the present invention comprises: a desulfurization apparatus for contacting a raw material gas comprising hydrogen and carbon monoxide with a desulfurizing agent comprising copper; and a synthesis apparatus for contacting the raw material gas treated by the desulfurization apparatus with an oxygenate-synthesis catalyst comprising rhodium.

The oxygenate production method of the present invention comprises: a desulfurization step where a raw material gas comprising hydrogen and carbon monoxide is contacted with a desulfurizing agent comprising copper; and a synthesis step where the raw material gas treated in the desulfurization step is contacted with an oxygenate-synthesis catalyst comprising rhodium.

In the present invention, the term "oxygenate" denotes a molecule composed of a carbon atom, a hydrogen atom and an oxygen atom, such as acetic acid, ethanol, acetaldehyde, methanol, propanol, methyl formate, ethyl formate, methyl acetate or ethyl acetate.

Effect of the Invention

According to the oxygenate production system of the present invention, the production of an oxygenate can be efficiently performed for a long term in spite of the use of a rhodium-containing catalyst.

EMBODIMENTS FOR CARRYING OUT THE INVENTION

Oxygenate Production System

Explanations are made hereinbelow on the oxygenate production system according to one embodiment of the present invention, referring to the annexed drawings.

Figure 1:
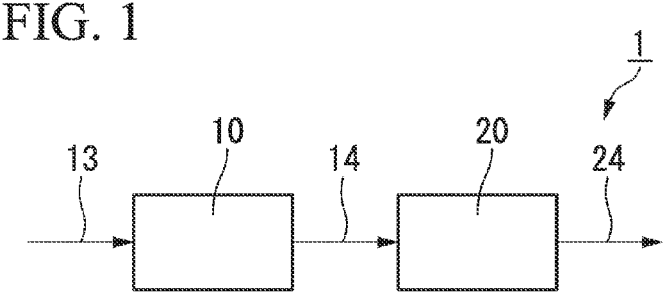
FIG. 1 is a schematic view of the oxygenate production system according to an embodiment of the present invention.

The oxygenate production system 1 shown in FIG. 1 comprises a desulfurization apparatus 10 and a synthesis apparatus 20. To the desulfurization apparatus 10 is connected a supply line 13 for raw material gas, which is connected with a supply source (not shown) for raw material gas. The desulfurization apparatus 10 and the synthesis apparatus 20 are connected to each other through a transfer line 14 for desulfurized gas, where a supply line 24 for synthesized gas is connected to the synthesis apparatus 20.

With respect to the source for the raw material gas, there is no limitation as long as it is capable of supplying a raw material gas comprising hydrogen and carbon monoxide (hereinafter, sometimes referred to simply as "raw material gas"). As examples of the source for the raw material gas, there can be mentioned a reservoir for storing the raw material gas and a gasification apparatus for gasifying organic materials such as biomass and plastics.

With respect to the gasification apparatus, there is no particular limitation as long as it can gasify organic materials to generate a raw material gas, and examples thereof include a fixed-bed gasification furnace, a fluidized-bed gasification furnace and an entrained-bed gasification furnace.

The supply line 13 for raw material gas is a part supplying a raw material gas to the desulfurization apparatus 10, and may be, for example, a pipe made of stainless steel etc.

The transfer line 14 for desulfurized gas is a part transferring a raw material gas treated in the desulfurization apparatus 10 to the synthesis apparatus, and may be, for example, a pipe made of stainless steel etc.

The transfer line 24 for synthesized gas is a part transferring a synthesized gas formed in the synthesis apparatus 20, and may be, for example, a pipe made of stainless steel etc.

With respect to the desulfurization apparatus 10, there is no limitation as long as it is capable of contacting the raw material gas with the desulfurizing agent comprising copper (hereinafter, sometimes simply referred to as "desulfurizing agent"). As an example of the desulfurization apparatus 10, there can be mentioned an apparatus having a reaction bed filled with a desulfurizing agent (hereinafter, sometimes also referred to as "desulfurization reaction bed"). The desulfurizing reaction bed may be either a fixed bed or a fluidized bed.

Explanations are made below with respect to an example of the desulfurization apparatus 10 referring to FIG. 2.

Figure 2:
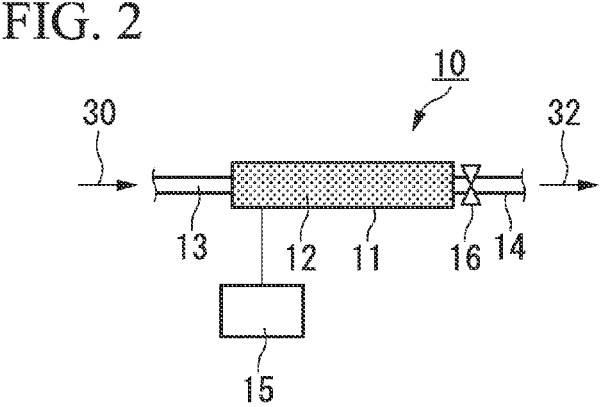
FIG. 2 is a schematic view of an example of the desulfurization apparatus.

The desulfurization apparatus 10 shown in FIG. 2 has a desulfurization reaction tube 11 which is filled with the desulfurizing agent and has formed therein a desulfurization reaction bed 12; a temperature control part 15 connected with the desulfurization reaction tube 11; and a pressure control part 16.

The desulfurization reaction tube 11 is preferred to be made of a material which is inert to the raw material gas and is preferred to have a shape such that the tube 11 can withstand a heating at around 100 to 500° C. and a pressure of around 10 MPa. As a specific example of the desulfurization reaction tube 11, there can be mentioned an approximately cylindrical part made of stainless steel.

With respect to the temperature control part 15, there is no particular limitation as long as it can control the temperature of the desulfurization reaction bed 12 in the desulfurization reaction tube 11 to a desired value, and examples of the temperature control part 15 include an electric furnace and the like.

With respect to the pressure control part 16, there is no particular limitation as long as it can control the internal pressure of the desulfurization reaction tube 11 to a desired value, and examples of the pressure control part 16 include a known pressure valve or the like which is provided at the desulfurized gas-transfer line 14.

The desulfurization apparatus 10 may be equipped with a known device such as a gas flow rate controller (e.g., mass flow controller) or the like which controls the flow rate of the raw material gas.

The desulfurizing agent contains copper. By the use of such a desulfurizing agent, it becomes possible to remove the sulfur content (sulfur and compounds thereof) from the raw material gas as much as possible, thereby enabling the suppression of time-dependent decrease in the activity of the oxygenate-synthesis catalyst mentioned below (hereinafter, sometimes referred to simply as "synthesis catalyst").

The desulfurizing agent may further contain a metal other than copper (optional metal for desulfurizing agent). Examples of the optional metal for desulfurizing agent include zinc, aluminum and chromium. These optional metals for desulfurizing agent may be used alone or in any combination of two or more thereof.

The optional metal for desulfurizing agent may be selected in view of the functions required of the desulfurizing agent etc. For example, the desulfurization efficiency of the desulfurizing agent can be increased by using zinc as the optional metal in combination with copper, while the heat stability of the desulfurizing agent can be increased by the use of aluminum as the optional metal in combination with copper.

The desulfurizing agent may be either in the form of an aggregate of copper and the optional metal for the desulfurizing agent or in the form of a supported catalyst in which copper and the optional metal are supported on a carrier. It is especially preferred to use an aggregate of copper and the optional metal as the desulfurizing agent. The use of an aggregate of copper and the optional metal for desulfurizing agent enables more efficient removal of the sulfur content from the raw material gas.

When the desulfurizing agent is in the form of the above-mentioned aggregate, the copper content of the desulfurizing agent is preferably in the range of from 5 to 60 mol %, more preferably from 7 to 52 mol %, still more preferably from 12 to 40 mol %. The copper content below the above-mentioned lower limit may result in a low desulfurizing effect, whereas the copper content above the above-mentioned upper limit may in some cases tend to cause a sintering of the copper.

When zinc is used as the optional metal for desulfurizing agent and the desulfurizing agent is used in the form of the above-mentioned aggregate, the zinc content of the desulfurizing agent is preferably in the range of from 5 to 60 mol %, more preferably from 10 to 45 mol %, still more preferably from 16 to 36 mol %. The zinc content below the above-mentioned lower limit may in some cases tend to cause sintering of copper, whereas the zinc content above the above-mentioned upper limit may result in a low desulfurizing effect.

With respect to the desulfurizing agent, the molar ratio of copper/zinc (hereinafter, sometimes referred to as "copper/zinc ratio") is preferably in the range of from 1/10 to 10/3, more preferably from 1/3 to 2/1, still more preferably from 1/2.3 to 1/1. When the copper/zinc ratio is within the above-mentioned range, the sulfur content can be more effectively removed from the raw material gas.

When aluminum is used as the optional metal for desulfurizing agent, the molar ratio of aluminum/copper (hereinafter, sometimes referred to as "aluminum/copper ratio) is preferably in the range of from 1/20 to 2/1, more preferably from 3/10 to 1/1. The aluminum/copper ratio below the above-mentioned lower limit may result in insufficient improvement of the heat resistance, whereas the aluminum/copper ratio above the above-mentioned upper limit may result in a low desulfurizing effect.

When chromium is used as the optional metal for desulfurizing agent, the desulfurizing agent may contain, for example, chromium oxide etc. in an amount up to 2 to 3% by weight.

The desulfurizing agent can be produced by any of the conventionally known methods for producing metal catalysts, such as a coprecipitation method and an immobilization method.

The method for producing the desulfurizing agent is explained below, taking the coprecipitation method as an example.

The production of the desulfurizing agent by the coprecipitation method can be carried out by forming a coprecipitate of a copper compound and a compound of the optional metal for the desulfurizing agent such as a zinc compound, followed by calcining the coprecipitate. The resultant desulfurizing agent is a mixture of a metallic copper and/or a copper oxide, and the optional metal for the desulfurizing agent and/or an oxide thereof.

Specifically, first, a copper compound and a compound of the optional metal for the desulfurizing agent are dissolved in water to obtain an aqueous solution of the metals. Then, the obtained aqueous solution of the metals and an aqueous solution of a precipitant are dropwise added to a purified water having an arbitrary temperature (for example, 60 to 90° C.) while stirring, to thereby form a precipitate. Alternatively, the aqueous solution of the metals may be dropwise added to an aqueous solution of a precipitant having an arbitrary temperature while stirring, to thereby form a precipitate. The obtained precipitate is washed with a purified water, followed by drying at an arbitrary temperature (for example, 100 to 150° C.) to obtain a dried product. The obtained dried product is calcined at an arbitrary temperature (for example, 250 to 350° C.) to obtain the desulfurizing agent.

With respect to the copper compound, there is no limitation as long as it is water-soluble, and examples thereof include a nitrate and an acetate. With respect to the compound of the optional metal for the desulfurizing agent, there is no limitation as long as it is water-soluble, and examples thereof include a nitrate and an acetate.

Examples of the aqueous solution of precipitant include an aqueous sodium carbonate solution and an aqueous potassium carbonate solution.

If necessary, the aqueous solution of precipitant may further contain 1 to 5% by weight of a known auxiliary shaping agent such as graphite.

The obtained desulfurizing agent can be activated by reduction treatment. (In the present specification, the operation to subject the desulfurizing agent to reduction treatment is sometimes referred to as "desulfurizing agent reduction operation".)

The desulfurizing agent reduction operation can be carried out, for example, by contacting the desulfurizing agent with a hydrogen-containing gas (reducing gas) at 150 to 300° C.

The reducing gas is a mixture of hydrogen and inert gas such as nitrogen. The hydrogen content of the reducing gas is not particularly limited, but is preferably 6% by volume or less, more preferably 0.5 to 4% by volume.

With respect to the synthesis apparatus 20, there is no limitation as long as it is capable of contacting the raw material gas treated by the desulfurizing apparatus 10 (hereinafter, sometimes referred to as "desulfurized gas") with an oxygenate-synthesis catalyst (hereafter, sometimes referred to simply as "synthesis catalyst"). As an example of the synthesis apparatus 20, there can be mentioned an apparatus having a reaction bed filled with the synthesis catalyst (hereinafter, sometimes referred to as "synthesis reaction bed"). The synthesis reaction bed may be either a fixed bed or a fluidized bed.

Explanations are made below with respect to an example of the synthesis apparatus 20 referring to FIG. 3.

Figure 3:
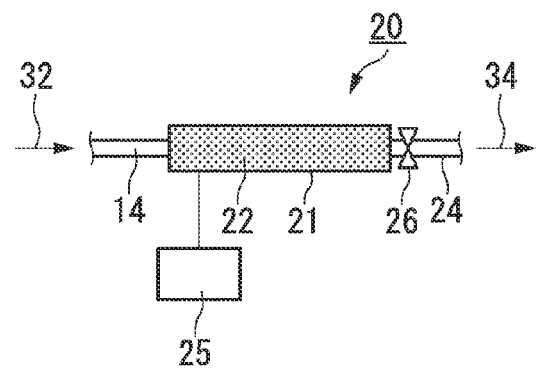
FIG. 3 is a schematic view of an example of the synthesis apparatus.

The synthesis apparatus 20 shown in FIG. 3 has a synthesis reaction tube 21 which is filled with the synthesis catalyst and has formed therein a synthesis reaction bed 22; a temperature control part 25 connected with the synthesis reaction tube 21; and a pressure control part 26.

The synthesis reaction tube 21 is preferred to be made of a material which is inert to the desulfurized gas and the synthesized oxygenate and is preferred to have a shape such that the tube 21 can withstand a heating at around 100 to 500° C. and a pressure of around 10 MPa. As a specific example of the synthesis reaction tube 21, there can be mentioned an approximately cylindrical part made of stainless steel.

With respect to the temperature control part 25, there is no particular limitation as long as it can control the temperature of the synthesis reaction bed 22 in the synthesis reaction tube 21 to a desired value, and examples of the temperature control part 25 include an electric furnace and the like.

With respect to the pressure control part 26, there is no particular limitation as long as it can control the internal pressure of the synthesis reaction tube 21 to a desired value, and examples of the pressure control part 26 include a known pressure valve or the like which is provided at the synthesized gas-transfer line 24.

The synthesis apparatus 20 may be equipped with a known device such as a gas flow rate controller (e.g., mass flow controller) or the like which controls a flow rate of the desulfurized gas.

The synthesis reaction bed 22 may be either one filled only with the synthesis catalyst or one filled with a mixture of the synthesis catalyst and a diluent such as silicon oxide. The use of silicon oxide in combination with the synthesis catalyst enables the suppression of overheating of the synthesis reaction bed 22.

The synthesis catalyst contains rhodium. Due to the presence of rhodium in the synthesis catalyst, an oxygenate can be efficiently produced from the desulfurized gas.

The synthesis catalyst may further contain a metal other than rhodium (hereinafter, sometimes referred to as optional metal for the synthesis catalyst) such as alkali metals and transition metals.

Examples of alkali metals include lithium, sodium and potassium. When the synthesis catalyst contains an alkali metal, the efficiency of the oxygenate synthesis can be improved. As the alkali metal, lithium is preferred. The use of lithium enables more efficient synthesis of an oxygenate by decreasing the by-product generation and increasing the CO conversion.

Herein, the term "CO conversion" means the molar percentage of the consumed CO relative to the total CO in the desulfurized gas.

Examples of transition metals include titanium, vanadium, chromium and manganese. When the synthesis catalyst contains a transition metal, the efficiency of the oxygenate synthesis can be improved. As the transition metal, manganese and titanium are preferred. When the synthesis catalyst contains manganese and/or titanium, an oxygenate can be synthesized more efficiently and the ethanol content of the oxygenate can also be increased.

As the synthesis catalyst, for examples, it is preferred to use a catalyst comprising rhodium and at least one metal selected from the group consisting of manganese and lithium, or a catalyst comprising rhodium, titanium and at least one metal selected from the group consisting of manganese and lithium. By the use of such a synthesis catalyst, an oxygenate can be synthesized more efficiently and the ethanol content of the oxygenate can also be increased.

The synthesis catalyst may be either in the form of an aggregate of rhodium and the optional metal for the synthesis catalyst or in the form of a supported catalyst in which rhodium and the optional metal are supported on a carrier. It is especially preferred to use a supported catalyst. By the use of a supported catalyst, rhodium and the optional metal for the synthesis catalyst can be more efficiently contacted with the desulfurized gas so that an oxygenate can be more efficiently produced.

When the synthesis catalyst is a supported catalyst and contains, as the optional metals, manganese, an alkali metal and titanium, it is preferred that the synthesis catalyst has a composition represented by the following formula (I):

$$aA \cdot bB \cdot cC \cdot dD \quad (I)$$

wherein A represents rhodium, B represents manganese, C represents an alkali metal, D represents titanium, a, b, c and d represent molar ratios, and a+b+c+d=1.

In the formula (I), a is preferably 0.053 to 0.98. When the value of a is below the above-mentioned lower limit, the content of rhodium is too low so that the efficiency of the oxygenate synthesis may not be sufficiently improved. When the value of a is above the above-mentioned upper limit, the contents of other metals are too low so that the efficiency of the oxygenate synthesis may not be sufficiently improved.

In the formula (I), the value of b is preferably 0.0006 to 0.67. When the value of b is below the above-mentioned lower limit, the content of manganese is too low so that the efficiency of the oxygenate synthesis may not be sufficiently improved. When the value of b is above the above-mentioned upper limit, the contents of other metals are too low so that the efficiency of the oxygenate synthesis may not be sufficiently improved.

In the formula (I), the value of c is preferably 0.00056 to 0.51. When the value of c is below the above-mentioned lower limit, the content of an alkali metal is too low so that the efficiency of the oxygenate synthesis may not be sufficiently improved. When the value of c is above the above-mentioned upper limit, the contents of other metals are too low so that the efficiency of the oxygenate synthesis may not be sufficiently improved.

In the formula (I), the value of d is preferably 0.0026 to 0.94. When the value of d is below the above-mentioned lower limit, the content of titanium is too low so that the efficiency of the oxygenate synthesis may not be sufficiently improved. When the value of d is above the above-mentioned upper limit, the contents of other metals are too low so that the efficiency of the oxygenate synthesis may not be sufficiently improved.

As the carrier, any of the known carriers used for metal catalysts can be used and examples thereof include silica, titania, alumina and ceria. Among these, silica is preferred from the viewpoints of increasing the selectivity of catalytic reaction and the CO conversion and because various silica products differing in specific surface area and pore size are commercially available.

Herein, the term "selectivity" means the molar percentage of the CO converted to the specific oxygenate relative to the consumed CO in the desulfurized gas. For example, according to the following formula (α), the selectivity for ethanol as the oxygenate is 100 mol %. On the other hand, according to the following formula (β), the selectivity for ethanol as the oxygenate is 50 mol % and the selectivity for acetaldehyde as the oxygenate is also 50 mol %.

$$4H_2+2CO \rightarrow CH_3CH_2OH+H_2O \quad (\alpha)$$

$$7H_2+4CO \rightarrow C_2H_5OH+CH_3CHO+2H_2O \quad (\beta)$$

As the carrier, it is preferred to use one having a specific surface area of 10 to 1,000 m²/g and a pore size of 1 nm or more.

In addition, it is preferred to use a carrier having a narrow particle size distribution. The average particle size of the carrier is not particularly limited but is preferably in the range of from 0.5 to 5,000 μm.

Various carriers are commercially available which differ in specific surface area, pore size, pore volume and particle size; therefore, the catalytic activity, the distribution of the products and the like can be adjusted by appropriately choosing the type of the carrier.

For example, in the case where a carrier having a small pore size is selected, it is considered that the catalytic activity or the distribution of the products changes due to factors such as decrease in the particle sizes of rhodium and the optional metal for the catalyst which are supported on the carrier, and lowering of the dissipation rates of the reaction gas and the products during the reaction by flowing the desulfurized gas.

When the synthesis catalyst is in the form of a supported catalyst, the total amount of the metals is preferably 0.01 to 10 parts by weight, more preferably 0.1 to 5 parts by weight, relative to 100 parts by weight of the carrier. When the total amount of the metals is below the above-mentioned lower limit, the efficiency of the oxygenate synthesis may become low. When the total amount of the metals is above the above-mentioned upper limit, the efficiency of the oxygenate synthesis may become low.

The synthesis catalyst can be produced by any of the conventionally known methods for producing metal catalysts. Examples of the method of producing the catalyst include impregnation, immersion, ion exchange, coprecipitation and kneading, and among these, the impregnation is preferred. When the impregnation is used, rhodium and the optional metal for the catalyst can be more evenly dispersed in the resultant catalyst, whereby the efficiency of the contact between the catalyst and the desulfurized gas is increased and, hence, the oxygenate can be more efficiently synthesized.

Examples of raw material compounds for rhodium and the optional metals used for preparing the catalyst include oxides; chlorides; inorganic salts such as nitrates and carbonates; organic salts or chelate compounds such as oxalates, acetylacetonate salts, dimethylglyoxime salts and ethylenediamine acetic acid salts; carbonyl compounds; cyclopentadienyl compounds; amine complexes; alkoxide compounds; and alkyl compounds, which are generally used as the compounds of the rhodium and the optional metals for preparing metal catalysts.

The catalyst production by the impregnation will be described below. First, the raw material compound(s) of rhodium (and the optional metals) is dissolved in a solvent such as water, methanol, ethanol, tetrahydrofuran, dioxane, hexane, benzene or toluene, and a carrier is, for example, immersed in the obtained solution (impregnation solution), thereby attaching the impregnation solution to the carrier. When a porous material is used as the carrier, after the impregnation solution sufficiently permeates the pores, the solvent is evaporated to obtain a catalyst.

Examples of the method of impregnating the carrier with the impregnation solution include a method (simultaneous method) of impregnating the carrier with a solution in which all raw material compounds have been dissolved, a method (sequential method) in which respective solutions of the raw material compounds are separately prepared and the carrier is sequentially impregnated with the solutions. Of these methods, the sequential method is preferred. By the use of the catalyst prepared by the sequential method, an oxygenate can be more efficiently produced.

The obtained synthesis catalyst can be activated by reduction treatment. (In the present specification, the operation to subject the synthesis catalyst to reduction treatment is sometimes referred to as "catalyst reduction operation".)

The catalyst reduction operation can be carried out, for example, by contacting the synthesis catalyst with reducing gas at preferably 200 to 600° C.

With respect to the heating time during the catalyst reduction operation, for example, the heating time is preferably 1 to 10 hours, and more preferably 2 to 5 hours.

(Oxygenate Production Method)

The oxygenate production method of the present invention comprises contacting a raw material gas with a desulfurizing agent (desulfurization step), followed by contacting with a synthesis catalyst (synthesis step). Explanations are made below with respect to an example of the oxygenate production method referring to FIGS. 1 to 3.

There is no limitation on the raw material gas 30 as long as it contains hydrogen and carbon monoxide. For example, the raw material gas 30 may be any one of a natural gas, a coal-derived gas, a biomass gas obtained by gasification of a biomass, and gas obtained by gasification of organic wastes such as waste plastics, waste papers and waste clothes. A biomass gas can be obtained by any of the conventional methods such as a method in which a pulverized biomass is heated in water vapor while heating at, for example, 800 to 1,000° C.

It is preferred that the raw material gas 30 is a gaseous mixture containing hydrogen and carbon monoxide as main components, namely a gaseous mixture wherein the total content of hydrogen and carbon monoxide is preferably 50% by volume or more, more preferably 80% by volume or more, still more preferably 90% by volume or more. The higher the contents of hydrogen and carbon monoxide in the raw material gas 30, the more oxygenate can be produced with higher efficiency.

The volume ratio of hydrogen to carbon monoxide (hereinafter, sometimes simply referred to as $H_2/CO$ ratio) is preferably 0.1 to 10, more preferably 0.5 to 3, still more preferably 1.5 to 2.5. When the $H_2/CO$ ratio is within the above-mentioned range, the stoichiometric balance is maintained within an appropriate range during the reaction producing an oxygenate in the below-described synthesis step, thereby enabling more efficient production of an oxygenate.

It is preferred that the amount of impurity in the raw material gas 30 is as small as possible.

However, a biomass gas or gas obtained by gasification of organic wastes such as waste plastics, waste papers and waste clothes (which are hereinafter sometimes collectively referred to as "recycle gas") contains methane, ethane, ethylene, nitrogen, carbon dioxide, water or a sulfur content (sulfur-containing compound) such as hydrogen sulfide ($H_2S$), carbonyl sulfide (COS), sulfur dioxide ($SO_2$) or thiophene ($C_4H_4S$). The sulfur content is generally present in the recycle gas in an amount of 10 to 100 ppm by volume and become a cause of lowering the activity of the synthesis catalyst at an early stage of the synthesis reaction.

Therefore, the raw material 30 is contacted with a desulfurizing agent in the desulfurization step to thereby remove the sulfur content from the raw material gas 30 as much as possible.

First, the temperature and pressure in the desulfurization reaction tube 11 of the desulfurization apparatus 10 are adjusted to predetermined values, and the raw material gas 30 is introduced into the desulfurization reaction tube 11 through the raw material gas supply line 13. The raw material gas 30 introduced into the desulfurization reaction tube 11 is flown within the desulfurization reaction bed 12 while being in contact with the desulfurizing agent, whereby the sulfur content is removed from the raw material gas 30 to obtain a desulfurized gas 32 (desulfurization step).

The temperature for the desulfurization step (desulfurization temperature), i.e., the temperature in the desulfurization reaction tube 11, is determined in view of the composition of the desulfurizing agent, the below-described desulfurization pressure, the flow rate of the raw material gas 30, the type of oxygenates to be obtained, etc. When it is intended to obtain ethanol as the oxygenate, for example, the desulfurization temperature can be appropriately determined within the range of from 50 to 400° C., preferably from 80 to 300° C., more preferably from 80 to 180° C., still more preferably from 80 to 150° C., especially preferably from 80 to 120° C., most preferably from 90 to 110° C. When the desulfurization temperature is not below the above-mentioned lower limit, the sulfur content of the raw material gas 30 can be more efficiently removed. When the desulfurization temperature does not exceed the above-mentioned upper limit, the generation of methanol as a side product can be suppressed.

The pressure for the desulfurization step (desulfurization pressure), i.e., the pressure in the desulfurization reaction tube 11, is determined in view of the composition of the desulfurization agent, the desulfurization temperature, the flow rate of the raw material gas 30, the type of oxygenates to be obtained, etc. The desulfurization pressure is, for example, preferably 0.1 to 5 MPa, more preferably 0.5 to 3 MPa. When the desulfurization pressure is not below the above-mentioned lower limit, the sulfur content of the raw material gas 30 can be more efficiently removed. When the desulfurization pressure does not exceed the above-mentioned upper limit, the pressure can be increased with less energy.

The desulfurization pressure may either be the same as or different from the below-described synthesis pressure. When the desulfurization pressure is the same as the synthesis pressure or is higher than the synthesis pressure by 0.01 to 0.6 MPa, the energy for pressure increase can be fully utilized.

The space velocity of the raw material gas 30 in the desulfurization reaction bed 12 (=SV (value obtained by dividing the gas supply rate (L) per unit time (h) by the amount of the desulfurizing agent (in terms of volume (L)) can be determined in view of the sulfur content of the raw material gas 30, the desulfurization temperature, the desulfurization pressure, the economy, etc. The SV of the raw material gas 30 in the desulfurization reaction bed 12 is preferably 100 to 5,000 $h^{-1}$, more preferably 500 to 2,000 $h^{-1}$ in terms of the values measured at standard conditions.

The sulfur content of the desulfurized gas 32 is preferably 10 ppb by volume or less, more preferably 1 ppb by volume or less, still more preferably 0.1 ppb by volume or less, or may be 0 ppb by volume. The lower the sulfur content of the desulfurized gas 32, the more the activity deterioration of the synthesis catalyst can be suppressed so that an oxygenate can be produced efficiently for a longer period of time.

While adjusting the temperature and pressure in the synthesis reaction tube 21 to predetermined values, the desulfurized gas 32 is introduced into the synthesis reaction tube 21 through the desulfurized gas supply line 14. The desulfurized gas 32 introduced into the synthesis reaction tube 21 is flown within the synthesis reaction bed 22 while being in contact with the synthesis catalyst, whereby a part of the gas is converted to an oxygenate, thus obtaining a synthesized gas 34 containing an oxygenate (synthesis step).

During the flow through the synthesis reaction bed 22, the desulfurized gas 32 forms an oxygenate, for example, via the catalytic reactions represented by the following formulae (1) to (5):

$$3H_2 + 2CO \rightarrow CH_3CHO + H_2O \quad (1)$$

$$4H_2 + 2CO \rightarrow CH_3CH_2OH + H_2O \quad (2)$$

$$H_2 + CH_3CHO \rightarrow CH_3CH_2OH \quad (3)$$

$$2H_2 + 2CO \rightarrow CH_3COOH \quad (4)$$

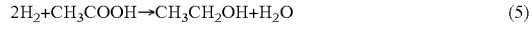
$$2H_2 + CH_3COOH \rightarrow CH_3CH_2OH + H_2O \quad (5)$$

The temperature for the synthesis step (synthesis temperature), i.e., the temperature in the synthesis reaction tube 21, is determined in view of the below-described synthesis pressure, the composition of the desulfurized gas 32, the type of oxygenates to be obtained, etc. The synthesis temperature is, for example, preferably 150 to 450° C., more preferably 200 to 400° C., still more preferably from 250 to 350° C. When the synthesis temperature is not below the above-mentioned lower limit, the rate of catalytic reaction can be sufficiently increased to enable more efficient production of an oxygenate. When the synthesis temperature does not exceed the above-mentioned upper limit, the oxygenate synthesis reaction predominantly proceeds to enable more efficient production of an oxygenate.

The pressure condition for the synthesis step (synthesis pressure), i.e., the pressure inside the synthesis reaction tube 21, is, for example, preferably 0.5 to 10 MPa, more preferably 1 to 7.5 MPa, more preferably 2 to 5 MPa. When the synthesis pressure is not below the above-mentioned lower limit, the rate of catalytic reaction can be sufficiently increased to enable more efficient production of an oxygenate. When the synthesis pressure does not exceed the above-mentioned upper limit, the oxygenate synthesis reaction predominantly proceeds to enable more efficient production of an oxygenate.

The space velocity of the desulfurized gas 32 in the synthesis reaction bed 22 (=SV (value obtained by dividing the gas supply rate (L) per unit time (h) by the amount of the synthesis catalyst (in terms of volume (L)) is preferably adjusted to be in the range of 10 to 100,000 $h^{-1}$ in terms of the values measured at standard conditions. The SV is appropriately adjusted in view of the reaction pressure, the reaction temperature and the composition of the raw material gas as the raw material, which are suited for an oxygenated to be obtained.

There is no particular limitation on the synthesized gas 34 as long as it contains an oxygenate, but the synthesized gas 34 preferably contains at least one compound selected from the group consisting of acetic acid, ethanol and acetaldehyde, more preferably contains ethanol. This is because, with such a synthesized gas 30, the synthesis catalyst can efficiently produce a C2 compound.

The selectivity for or yield of the oxygenate can be controlled by adjusting the synthesis temperature, the synthesis pressure, the SV of the desulfurized gas 32 in the synthesis reaction bed 22, and the like.

If necessary, the synthesized gas 34 withdrawn from the synthesis gas transfer line 24 may be treated with a gas-liquid separator or the like, to thereby separate the gas into unreacted desulfurized gas 32 and an oxygenate.

When a recycle gas is used as the raw material gas 30, before being introduced into the desulfurization reaction tube 11, the gas 30 may be subjected to a treatment for removing impurities other than the sulfur content, such as a tar content, a nitrogen content, a chlorine content, and moisture.

If necessary, other desulfurization apparatus (hereinafter, sometimes referred to as a "primary desulfurization apparatus") may be provided upstream of the desulfurization apparatus 10. Examples of primary desulfurization apparatuses include an apparatus having a reaction bed filled with a known desulfurizing agent containing no copper (non-copper desulfurizing agent) such as zinc oxide; an apparatus having a reaction bed filled with a cobalt-molybdenum (Co—Mo) catalyst or a nickel-molybdenum (Ni—Mo) catalyst and, at a downstream portion thereof, a non-copper desulfurizing agent; and a PSA apparatus. The reaction bed filled with a non-copper desulfurizing agent or a combination of a non-copper desulfurizing agent with a Co—Mo catalyst or a Ni—Mo catalyst may be provided at an upstream portion within the desulfurization reaction tube 11 of the desulfurization apparatus 10. When such a primary desulfurization apparatus is provided, the sulfur content of the raw material gas 30 can be reduced to 10 ppm by volume or less. By reducing, in advance, the sulfur content of the raw material gas 30 to 10 ppm by volume or less, the efficiency of desulfurization exerted by the desulfurizing agent in the desulfurization apparatus 10 can be further enhanced so that the sulfur content of the raw material gas 30 can be removed as much as possible for a long time while reducing the load on the desulfurizing agent.

After the synthesis step, there may be provided a step for hydrogenating products other than ethanol (e.g., C2 compounds except for ethanol, such as acetic acid and acetaldehyde, and esters such as ethyl acetate, methyl acetate and methyl formate) to convert such products into ethanol (ethanolification step). The ethanolification step can be carried out, for example, by a method in which oxygenates including acetaldehyde, acetic acid, etc. are contacted with a hydrogenation catalyst to convert the oxygenates into ethanol.

Herein, as the hydrogenation catalyst, catalysts known in the related art can be used, and examples thereof include copper, copper-zinc, copper-chromium, copper-zinc-chromium, iron, rhodium-iron, rhodium-molybdenum, palladium, palladium-iron, palladium-molybdenum, iridium-iron, rhodium-iridium-iron, iridium-molybdenum, rhenium-zinc, platinum, nickel, cobalt, ruthenium, rhodium oxide, palladium oxide, platinum oxide and ruthenium oxide. These hydrogenation catalysts may be a supported catalysts supported by the same carrier as is usable for the synthesis catalyst used in the present invention, and the preferred supported catalyst is a copper-type catalyst in which copper, copper-zinc, copper-chromium or copper-zinc-chromium is supported on a silica-type carrier. Examples of the method of producing the hydrogenation catalyst in the form of a supported catalyst include the simultaneous method or the sequential method as in the case of the synthesis catalyst.

Alternatively, for obtaining acetaldehyde with high efficiency, there may be provided a step where the products are treated with a gas-liquid separator or the like to recover ethanol, which is then oxidized to be converted into acetaldehyde.

As the method of oxidizing ethanol, there can be mentioned a method in which ethanol after being liquefied or gasified is contacted with an oxidation catalyst such as a metal catalyst composed mainly of gold, platinum, ruthenium, copper or manganese, or a metal alloy catalyst comprising two or more of the above-mentioned metals. These oxidation catalysts may be in the form of supported catalysts, each comprising a metal supported by the same support as is usable for the synthesis catalyst.

With respect to the conventionally known desulfurization methods such as PSA method or a method using zinc oxide as a desulfurizing agent, the sulfur content of the raw material gas could not be sufficiently reduced by such methods. When a raw material gas having a high sulfur content is contacted with a synthesis catalyst, the activity of the catalyst is decreased at an early stage. In addition, the desulfurizing agent conventionally used for removing sulfur content from natural gas or petroleum preferentially synthesizes methane from a raw material gas containing hydrogen and carbon monoxide and, hence, cannot be used for efficiently producing an oxygenate.

Further, when the desulfurization is carried out by a wet method, it becomes difficult to control the water content of the desulfurized gas, so that an efficient production of the targeted oxygenate becomes difficult.

The oxygenate production system and the oxygenate production method of the present invention utilize a desulfurizing agent containing copper, so that the sulfur content of the raw material gas can be removed as much as possible preferentially over the synthesis of methane. Therefore, the lowering of activity of the synthesis catalyst can be suppressed, and the oxygenate can be produced efficiently for a long time.

EXAMPLES

Hereinbelow, the present invention will be described with reference to the examples which, however, should not be construed as limiting the present invention.

(Preparation Example 1) Preparation of Desulfurizing Agent

An aqueous metal solution containing 0.5 mol/L of copper nitrate and 0.5 ml/L of zinc nitrate was prepared. To an aqueous sodium carbonate solution (concentration: 0.6 mol/L) having a temperature of 60° C. was dropwise added the above-mentioned aqueous metal solution while stirring, to thereby form a precipitate. The formed precipitate was recovered by filtration, followed by washing with water. The washed precipitate was pelletized into a cylindrical tablet having a height of ⅛ inch (0.32 cm) and a diameter of ⅛ inch (0.32 cm), followed by calcination at 300° C., to thereby obtain a desulfurizing agent.

The obtained desulfurizing agent was contacted with a nitrogen gas containing 2% by volume of hydrogen at 200° C., thereby performing a reduction treatment.

(Preparation Example 2) Preparation of Synthesis Catalyst 0.61 mL of an aqueous solution containing 0.0123 g of titanium lactate ammonium salt $(Ti(OH)_2[(OCH(CH_3)COO^-)]_2(NH_4^+)_2$ was dropwise added to 1.0 g of a silica gel (specific surface area: 430 $m^2$/g, average pore diameter: 5.7 nm, pore volume: 0.61 $cm^3$/g), to thereby impregnate the silica gel with the aqueous solution. The resultant was dried at 110° C. for 3 hours, followed by calcination at 400° C. for 3 hours, thereby obtaining a primary supported body. 0.61 mL of an aqueous solution containing 0.0768 g of rhodium chloride trihydrate ($RhCl_3.3H_2O$), 0.0048 g of lithium chloride monohydrate ($LiCl.H_2O$) and 0.0433 g of manganese chloride tetrahydrate ($MnCl_2.4H_2O$) is dropwise added to the primary supported body to thereby impregnate the primary supported body with the aqueous solution. The resultant was heated at 110° C. for 3 hours, followed by calcination at 400° C. for 3 hours, thereby obtaining a synthesis catalyst. With respect to the obtained synthesis catalyst, it was found that the ratio of supported rhodium=3% by weight/$SiO_2$, and Rh:Mn:Li:Ti=0.461:0.346:0.127:0.066 (molar ratio).

Experimental Example 1

7.9 g of the desulfurizing agent obtained in Preparation Example 1 was charged into a cylindrical reaction tube made of stainless steel and having an inner diameter of 10.7 mm and a length of 40 cm, to thereby form a desulfurization reaction bed. A reduction treatment was carried out by heating at 320° C. for 2 hours while flowing a reduction gas (hydrogen content: 30% by volume) under normal pressure through the desulfurization reaction bed at SV=1,000 $h^{-1}$.

A raw material gas ($H_2$/CO ratio=2, no sulfur content) was flown through the desulfurization reaction bed at SV=1,500 $h^{-1}$ at reaction temperatures of 100° C., 120° C., 150° C., 180° C., 200° C. and 280° C. under a reaction pressure of 0.9 MPa, to thereby obtain a desulfurized gas.

Figure 4:
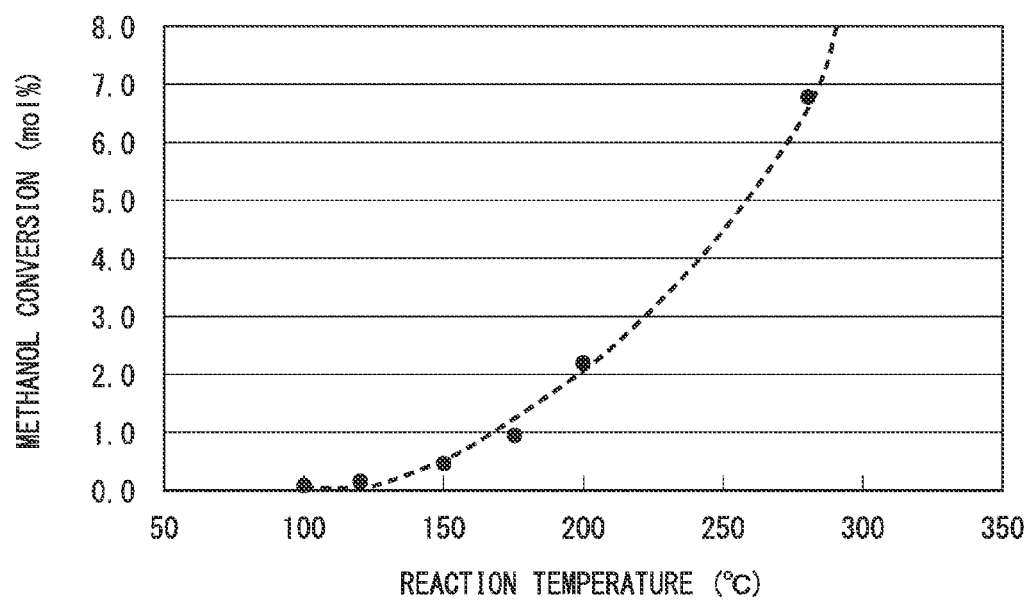
FIG. 4 is a graph showing the results of Experimental Example 1.

At each of the respective temperatures, the raw material gas was flown through the desulfurization reaction bed for 1 hour. The gas which had been flown through the desulfurization reaction bed was recovered and analyzed by gas chromatography. From the obtained data, the methanol conversion (mol %) was calculated. The results are shown in FIG. 4. The methanol conversion is a molar percentage of CO consumed for methanol synthesis relative to the total CO in the raw material gas.

FIG. 4 is a graph wherein the ordinate shows the methanol conversion values and the abscissa shows the reaction temperatures.

As shown in FIG. 4, the methanol conversion decreased as the reaction temperature became lower. At reaction temperatures below 180° C., the methanol conversion was 1 mol % or less.

Example 1

Figure 5:
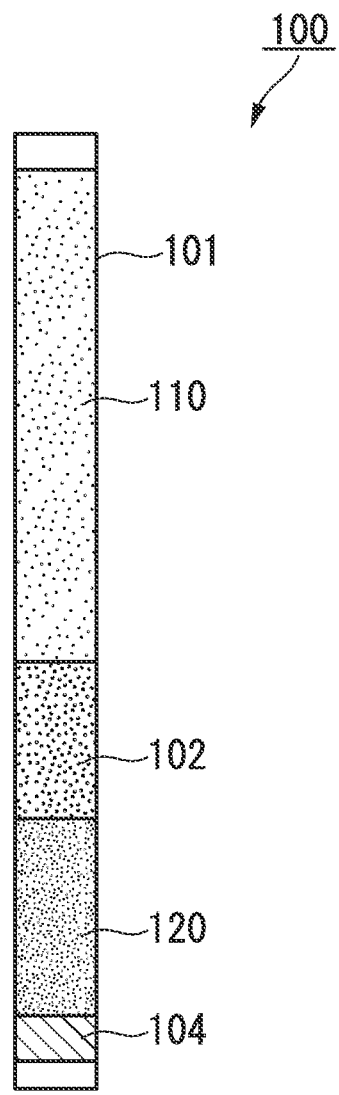
FIG. 5 is a schematic view of the oxygenate production system used in Example 1.

The oxygenate production system 100 shown in FIG. 5 was produced. The oxygenate production system 100 has a cylindrical reaction tube 101 made of stainless steel (inner diameter; 10.7 mm), in which a desulfurization reaction bed 110, a silicon oxide layer 102, a synthesis reaction bed 120 and a perforated plate 104 are laminated in this order from a vertically upward direction.

The desulfurization reaction bed 110 as a desulfurization apparatus is a layer (length: 11.5 cm) which is filled with 12.9 g of the desulfurizing agent prepared in Preparation Example 1, and the synthesis reaction bed 120 as a synthesis apparatus is a layer (length: 4 cm) which is filled with a mixture of 0.5 g of the synthesis catalyst prepared in Preparation Example 2 and 2.5 g of silicon oxide. The silicon oxide layer 102 is a layer (length: 4 cm) which is filled with 5 g of silicon oxide. The perforated plate 104 is a punched metal made of stainless steel and having a plurality of holes of $\varphi$0.5 mm.

The desulfurizing agent and the synthesis catalyst were subjected to reduction treatment by flowing a reduction gas (hydrogen concentration: 30% by volume) in the reaction tube 101 at SV=1,800 h$^{-1}$ under normal pressure while increasing the temperature in the reaction tube 101 from room temperature (25° C.) to 320° C. over 80 minutes and, then, maintaining the temperature at 320° C. for 2 hours.

The temperature within the reaction tube was set at 280° C. and a raw material gas ($H_2$:CO:$N_2$=6:3:1; $H_2S$ concentration=0.1 ppm by volume) was introduced from the upper end of the oxygenate production system 100 at SV=1,500 h$^{-1}$ to the desulfurization reaction bed 110 and at SV=9,000 h$^{-1}$ to the synthesis reaction bed 120. The pressure within the reaction tube 101 was 0.9 MPa. When a given period of time had passed since introduction of the raw material gas, the synthesized gas containing products which had been withdrawn from the oxygenate production system 100 was recovered and analyzed by gas chromatography.

Figure 6:
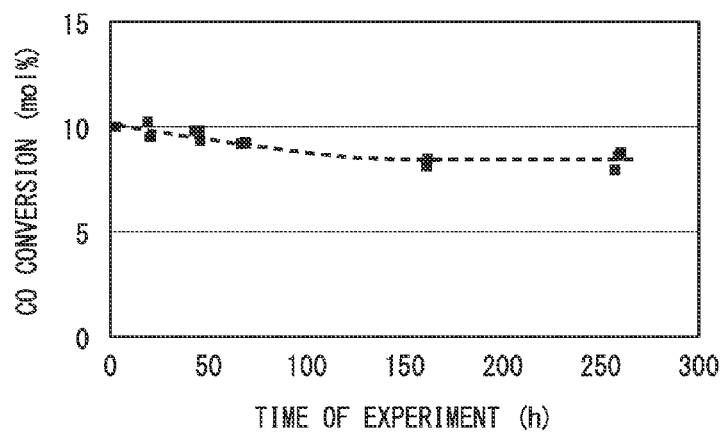
FIG. 6 is a graph showing the results of Example 1.

From the obtained data, the CO conversion (mol %) was calculated. The results are shown in FIG. 6.

Here, the methanol formed in the desulfurization reaction bed was excluded from the calculation of the conversion.

With respect to the $H_2S$ concentration (0.1 ppm by volume), this concentration was determined on the assumption that the raw material gas was treated by the conventional desulfurization method (PSA method, contact with a non-copper desulfurizing agent, etc.).

Comparative Example 1

Figure 7:
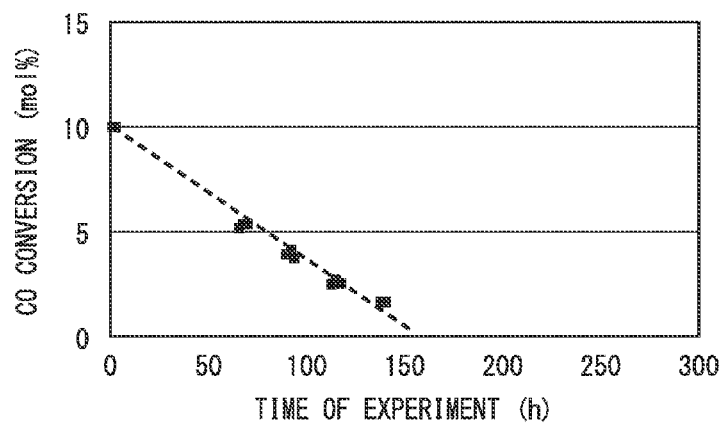
FIG. 7 is a graph showing the results of Comparative Example 1.

The same procedures as in Example 1 were repeated except that a desulfurization reaction bed was not provided, to thereby obtain CO conversion. The results are shown in FIG. 7.

Reference Example 1

The same procedures as in Comparative Example 1 were repeated except that a raw material gas containing no $H_2S$ ($H_2$:CO:$N_2$=6:3:1) was used, to thereby obtain CO conversion. The results are shown in FIG. 8.

As shown in FIG. 6, in Example 1 according to the present invention, the CO conversion immediately after the initiation of flow of the raw material gas was 10 mol % and the CO conversion at 260 hours after the initiation of flow of the raw material gas was 8.7 mol %.

As shown in FIG. 7, in Comparative Example 1 where a desulfurization reaction bed was not provided, the CO conversion immediately after the initiation of flow of the raw material gas was 10 mol % and the CO conversion at 140 hours after the initiation of flow of the raw material gas was 1.6 mol %.

Figure 8:
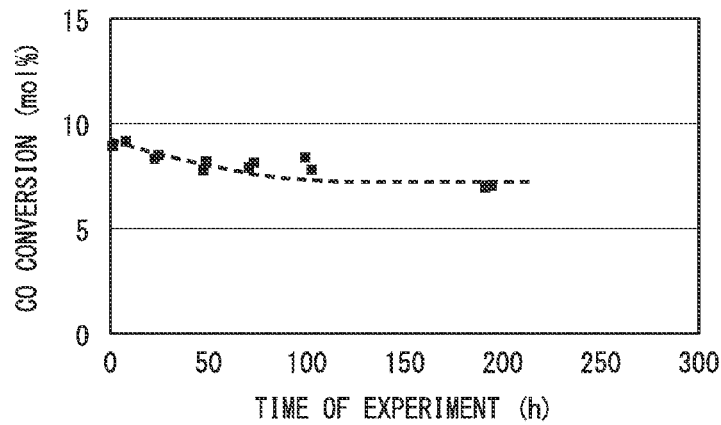
FIG. 8 is a graph showing the results of Reference Example 1.

As shown in FIG. 8, in Reference Example 1 where a raw material gas containing no $H_2S$ was used, the CO conversion immediately after the initiation of flow of the raw material gas was 9.0 mol % and the CO conversion at 200 hours after the initiation of flow of the raw material gas was 7.0 mol %.

With respect to the selectivities for the main components relative to the converted CO in Example 1, Comparative Example 1 and Reference Example 1, the selectivity for ethanol was 28 to 35 mol %, the selectivity for acetaldehyde was 20 to 25 mol % and the selectivity for methane was 30 to 35 mol %. Here, the methanol formed in the desulfurization reaction bed 110 was excluded from the calculations of the selectivities.

From comparison between Comparative Example 1 and Reference Example 1, it was found that the CO conversion decreases with the lapse of time when a raw material gas containing sulfur content is used.

From comparison between Example 1 and Comparative Example 1, it was found that, by the present invention, the activity of the synthesis catalyst can be maintained and an oxygenate can be efficiently produced for a long period of time.

Further, when the sulfur content was measured by a semiconductor type infrared absorption method with respect to the synthesis catalyst withdrawn from the upper layer of the synthesis reaction bed used in Example 1, it was found that the sulfur content was below the detection limit (0.01 ppm by weight). From this, it is presumed that the hydrogen sulfide content of the raw material gas was reduced to less than 1 ppb by volume by the flow of the raw material gas through the desulfurization reaction bed.

Example 2

Figure 9:
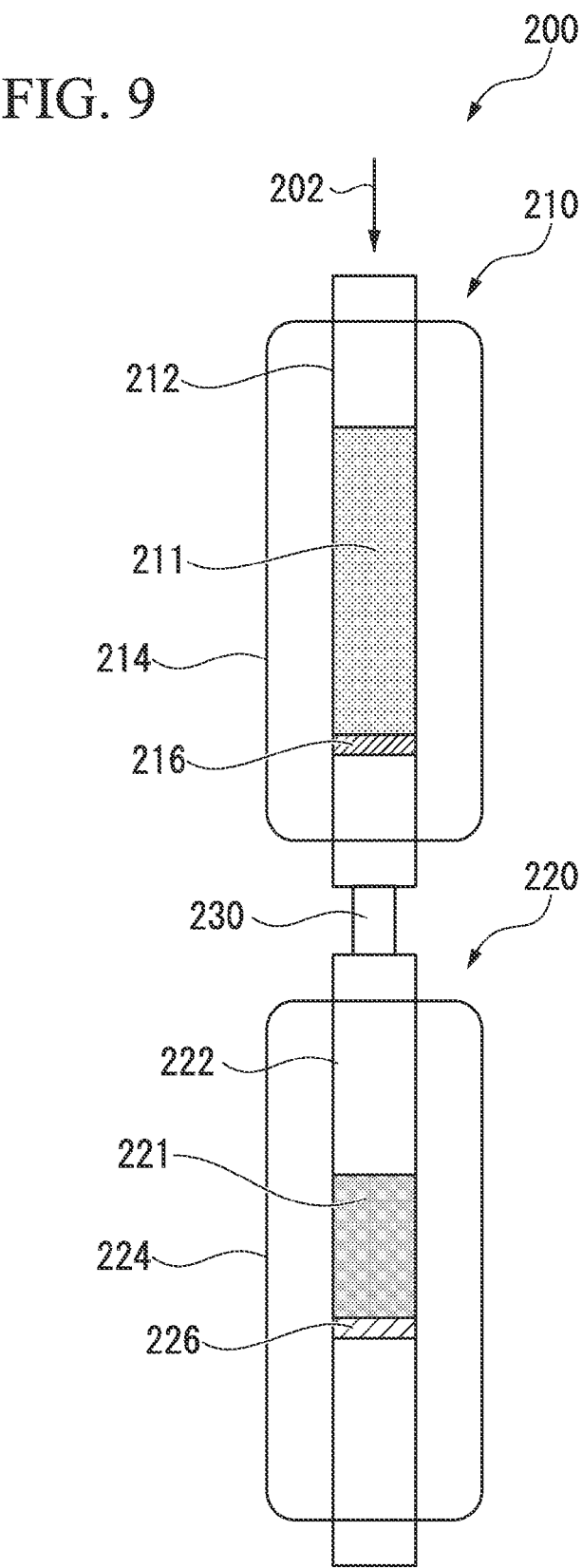
FIG. 9 is a schematic view of the oxygenate production system used in Example 2.

The oxygenate production system 200 shown in FIG. 9 was produced. The oxygenate production system 200 has a desulfurization apparatus 210 and a synthesis apparatus 220 which are connected via a desulfurized gas transfer line 230.

The desulfurization apparatus 210 has a cylindrical reaction tube 212 made of stainless steel (inner diameter: 10.7 mm) and a heating part 214 covering the reaction tube 212. In the reaction tube 212 is provided a perforated plate 216 on which is formed a desulfurization reaction bed 211.

The desulfurization reaction bed 211 is a layer (length: 5.1 cm) which is filled with 5.4 g of the desulfurizing agent prepared in Preparation Example 1.

The synthesis apparatus 220 has a cylindrical reaction tube 222 made of stainless steel (inner diameter: 10.7 mm) and a heating part 224 covering the reaction tube 222. In the reaction tube 222 is provided a perforated plate 226 on which is formed a synthesis reaction bed 221.

The synthesis reaction bed 221 is a layer (length: 4 cm) which is filled with a mixture of 0.5 g of the synthesis catalyst prepared in Preparation Example 2 and 2.5 g of silicon oxide.

Each of the perforated plates 216,226 is a punched metal made of stainless steel and having φ0.5 mm holes.

A hydrogen gas was flown through the inside of the oxygenate production system 200 along the direction of the arrow 202 under normal pressure at SV=450 h$^{-1}$ (desulfurization reaction bed) and at SV=1,800 h$^{-1}$ (synthesis reaction bed), while increasing the temperature in the reaction tube 212 from room temperature (25° C.) to 100° C. over 90 minutes and increasing the temperature in the reaction tube 222 from room temperature to 260° C. over 90 minutes.

Then, a raw material gas ($H_2$:CO:$N_2$=6:3:1, $H_2S$ concentration=0.1 ppm by volume, COS concentration=0.1 ppm by volume) was introduced from the upper end of the reaction tube 212 along the direction of the arrow 202, so that SV=3,000 h$^{-1}$ for the desulfurization reaction bed 211 and SV=12,000 h$^{-1}$ for the synthesis reaction bed 221. Here, the pressure within the reaction tube 212 was set at 2.0 MPa and the pressure within the reaction tube 222 was set at 2.0 MPa.

When a given period of time had passed since introduction of the raw material gas, the synthesized gas containing products which had been withdrawn from the oxygenate production system 200 was recovered and analyzed by gas chromatography.

From the obtained data, the CO conversion (mol %) was calculated. The results are shown in FIG. 10.

With respect to each of the $H_2S$ concentration and the COS concentration, the concentration was determined on the assumption that the raw material gas was treated by the conventional desulfurization method (PSA method, contact with a non-copper desulfurizing agent, etc.).

Figure 10:
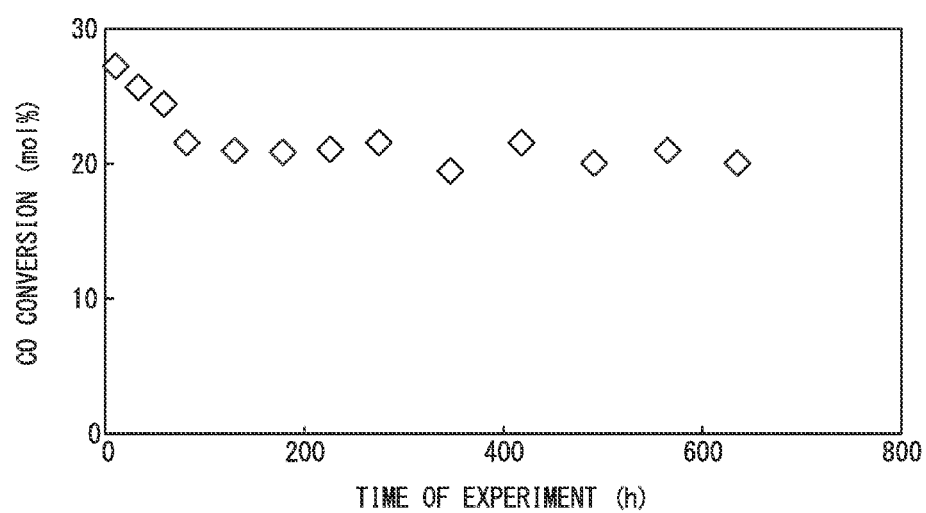
FIG. 10 is a graph showing the results of Example 2.

As shown in FIG. 10, in Example 2 according to the present invention, the CO conversion immediately after the initiation of flow of the raw material gas was 27 mol %, the CO conversion at 84 hours after the initiation of flow of the raw material gas was 22 mol %, and the CO conversion at 636 hours after the initiation of flow of the raw material gas was 20 mol %.

With respect to the selectivities for the main components relative to the converted CO, the selectivity for ethanol was 35 to 40 mol %, the selectivity for acetaldehyde was 40 to 45 mol % and the selectivity for methane was 10 to 15 mol %. Further, the selectivity for methanol was less than 1 mol %.

When the sulfur content (weight of the element S) of the desulfurizing agent after the experiment was measured by the semiconductor type infrared absorption method, it was found that the sulfur content was 2.2 mg in 5.4 g of the desulfurizing agent. Since the sulfur content ($H_2S$, COS) of the raw material gas was 0.2 ppm by volume and the flow amount of the raw material gas was [200 mL/min×636 hours], the amount of sulfur components flown (weight of the element S) was 2.2 mg. This indicates that almost all of the sulfur components in the raw material gas were adsorption-removed by the desulfurization reaction bed.

Further, when the temperature of the desulfurization reaction bed was increased to 120° C. which is higher than the temperature (100° C.) in this experiment, the amount of methanol formed by the desulfurizing agent was higher than this experiment.

Thus, it was found that, by the present invention, the activity of the synthesis catalyst can be maintained and an oxygenate can be efficiently produced for a long period of time.

The preferred examples of the present invention are explained above; however, the present invention should not be limited to these examples. Various alterations such as addition, omission and substitution of any components, etc. may be made as long as such alterations do not deviate from the gist of the present invention. The present invention should not be limited by the above explanations and is limited only by the annexed claims.

DESCRIPTION OF THE REFERENCE SIGNS 1, 100, 200 Oxygenate production system
10, 210 Desulfurization apparatus
20, 220 Synthesis apparatus
11 Desulfurization reaction tube
12, 110, 211 Desulfurization reaction bed
13 Raw material gas supply line
14, 230 Desulfurized gas transfer line
15, 25 Temperature control part
16, 26 Pressure control part
21 Synthesis reaction tube
22, 120, 221 Synthesis reaction bed
24 Synthesized gas transfer line
30 Raw material gas
32 Desulfurized gas
34 Synthesized gas
101, 212 Reaction tube
102 Silicon oxide layer
104, 216, 226 Perforated plate
214, 224 Heating portion

The invention claimed is:

1. A method for producing an oxygenate, comprising:
a desulfurizing agent-preparation step, wherein:
(1) a copper compound, zinc compound and optionally a compound of at least one metal selected from the group consisting of aluminum and chromium are dissolved in water to obtain an aqueous solution of metals,
(2) the obtained aqueous solution of metals and an aqueous solution of a precipitant are dropwise added to a purified water having a temperature of 60 to 90° C. while stirring to thereby form a precipitate, or the aqueous solution of metals is dropwise added to an aqueous solution of a precipitant having a temperature of 60 to 90° C. while stirring to thereby form a precipitate,
(3) the obtained precipitate is washed with a purified water, followed by drying at 100 to 150° C. to obtain a dried product, and
(4) the obtained dried product is calcined at 250 to 350° C. to obtain a desulfurizing agent having a molar ratio of copper/zinc of 1/2.3 to 1/1;
a desulfurization step wherein a raw material gas comprising hydrogen and carbon monoxide is contacted with the desulfurizing agent at a temperature of 120 to 180° C.; and
a synthesis step wherein the raw material gas treated in the desulfurization step is contacted with an oxygenate-synthesis catalyst of the following formula (I):

$$aA \cdot bB \cdot cC \cdot dD \qquad (I)$$

wherein A represents rhodium, B represents manganese, C represents an alkali metal, and D represents titanium, and
a, b, c and d represent molar ratios wherein a is 0.053 to 0.98, b is 0.0006 to 0.67, c is 0.00056 to 0.51, and d is 0.0026 to 0.94, with the proviso that a+b+c+d=1.

2. The method according to claim 1, wherein in the desulfurization step, the raw material gas is contacted with the desulfurizing agent at a temperature of from 150 to 180° C.

* * * * *